United States Patent [19]
Wang et al.

[11] Patent Number: 5,473,084
[45] Date of Patent: Dec. 5, 1995

[54] CHLORINATION PROCESS WITH HIGH PARA SELECTIVITY

[75] Inventors: Shian-Jy Wang, Hsinchu; Po-Yu Chen, Tauryuan; Ying-Tse Chuang; Wen-Chyi Lin, both of Hsinchu, all of Taiwan

[73] Assignee: Industrial Technology Research Institute, Hsinchu, Taiwan

[21] Appl. No.: 71,445

[22] Filed: Jun. 2, 1993

[51] Int. Cl.$^6$ .................... C07C 25/06; C07D 213/61
[52] U.S. Cl. .................................... 546/345; 570/208
[58] Field of Search .................. 546/345; 570/208

[56] References Cited

FOREIGN PATENT DOCUMENTS 0112722  7/1984  European Pat. Off. ............ 570/208

*Primary Examiner*—Alan L. Rotman
*Attorney, Agent, or Firm*—W. Wayne Liauh

[57] ABSTRACT

A heterogeneous catalytic chlorination process for making chlorinated aromatic compounds with high para-selectivity. Examples of chlorinated aromatic compounds that can be prepared using the process disclosed in the present invention include those compounds represented by the following formula:

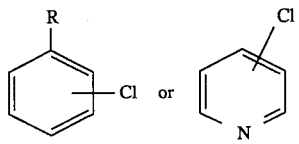

wherein R can be a C1–C3 alkyl, floride, chloride, bromide, iodide, or hydroxyl group. The chlorination process utilizes a de-aluminated zeolite which is prepared by $H_4$ EDTA or $Na_4$ EDTA extraction of L-type zeolite to reduce the alumina content thereof. The $SiO_2/Al_2O_3$ ratio of the de-aluminated zeolite is preferably between about 9 and about 40. The de-aluminated zeolite can be ion-exchanged with Group IA or IIA metal ions to further improve its para-selectivity.

16 Claims, No Drawings

1

CHLORINATION PROCESS WITH HIGH PARA SELECTIVITY

FIELD OF THE INVENTION

This invention relates to a process for making chlorinated aromatic compounds with high para selectivity. More particularly, this invention relates to a heterogeneous catalytic chlorination process for making chlorinated aromatic compounds, such as benzene, phenol, pyrindine, etc., with high para selectivity.

BACKGROUND OF THE INVENTION

Chlorinated aromatic compounds are generally used as solvents or raw materials in the manufacturing of medicinal and agricultural chemicals. For example, para-chlorotoluene is used in making pesticides and synthetic dyes, and para-dichlorobenzene in the making of synthetic dyes and moth control agents. More recently, para-dichlorobenzene is also used as raw material in making poly(phenylene sulfide), an important engineering plastics. Such new applications have resulted in the continuous increase in the demand for chlorinated aromatic compounds, especially the para-chlorinated products.

Conventionally, chlorinated aromatic compounds are made with liquid phase chlorination processes using homogeneous Lewis acids as catalysts. Examples of the Lewis acids for catalyzing the chlorination reaction between benzene rings and chlorine include $SbCl_5$, $FeCl_3$, and $AlCl_3$, etc. The conventional chlorination reaction utilizing Lewis acid as catalyst is often conducted at approximately one atmosphere pressure and 60° C. in a batch reactor lined with corrosion-resistant material such as Teflon. The conventional chlorination process, however, has poor para selectivity and the chlorinated products often contain mixtures of ortho- and para-products. Sometimes, the products also contain polychlorobenzene as by-products. Typically, the para selectivity in the production of para-chlorotoluene is about 50–55%. The para selectivity in the production of dichlorobenzene from the convention process is slightly better at about 60–70%.

With the increasing concern over environmental pollution, the convention chlorination process suffers another shortcoming in that, after the chlorination reaction, it is often necessary to add large amounts of water to the reaction mixture to neutralize the Lewis acid catalyst in order to separate the organic layer (containing reaction products) from the aqueous layer (containing catalysts). This not only results in the dilution of the catalyst thus rendering it unrecyclable, it also creates waste water/waste acid disposal problems.

U.S. Pat. No. 4,327,036 (the '036 patent) discloses a liquid phase chlorination process using dichlorine monoxide as the chlorination agent. Acetic acid, trichloroacetic acid, or trifluoroacetic acid is used as catalyst. The '036 patent does not address the issue of para selectivity. For example, in the chlorination of toluene, the product is primarily pentachlorotoluene. In the chlorination of chlorobenzene, the calculated para selectivity is only 60%.

A number of prior art disclosures have taught various heterogeneous catalytic chlorination processes which utilized various zeolites as catalysts for the chlorination of benzene rings. Zeolites are crystalline aluminosilicates of Group IA and Group IIA elements such as sodium, potassium, magnesium, and calcium. Chemically speaking, zeolites are represented by the empirical formula: $M_{x/n} \cdot xAlO_2 \cdot ySiO_2 \cdot wH_2O$, wherein M is a Group IA or Group IIA metal, n is the valence of the cation, x and y are an integer of 2 or greater, and w represents the water contained in the voids of the zeolite.

Japanese Pat. Pub. No. 77631 discloses a process using X-type zeolite as a catalyst in the gas phase chlorination reaction to make dichlorobenzene. The conversion of chlorobenzene was only 48.3%. Euo. Pat. Pub. No. 112,722 ('722 patent) discloses a process which used X-type zeolite as a catalyst in a liquid phase chlorination reaction of toluene. In a batch process, the convention of toluene was only 85%, and the selectivity of para-chlorotoluene was only 34.7%. Y-type zeolite has also been disclosed in the prior art as a catalyst in the liquid phase chlorination reaction to make dichlorobenzene. However, the selectivity of para-dichlorobenzene was only 71.8%. Both the X-type and Y-type zeolites are synthetic zeolites. The X-type zeolite is typically represented by a formula having a $AlO_2/SiO_2$ ratio of about 86:106; whereas, the Y-type zeolite is typically represented by a formula having a relatively lower $AlO2/SiO_2$ ratio of about 86:136.

In addition to the X-type and Y-type zeolites, L-type zeolite has also been disclosed in the prior art as a catalyst in the chlorination of benzene rings. The L-type zeolite is also a synthetic zeolite typically represented by the following formula:

$$K_9[(AlO_2)_9(SiO_2)_{27}] \cdot 22H_2O$$

As disclosed in Euo. Pat. Pub. No. 112,722, when an L-type zeolite was used in the chlorination of toluene, the conversion obtained was improved to 97.9%, and the ratio of parachlorotoluene/ortho-chlorotouluene was 0.5 (indicating a para selectivity of less than 33.3%). When an L-type zeolite was used in the chlorination of chlorobenzene, the conversion obtained was 85.6%, and the ratio of para-dichlorobenzene/ortho-dichlorobenzene was 0.124 (indicating a para selectivity of less than 11.0%).

Euo. Pat. Pub. No. 154,236 discloses a co-catalyst composition containing an aliphatic carboxylic acid and a zeolite catalyst to improve the conversion and para selectivity during the chlorination reaction. Specific examples include a co-catalyst composition containing L-type zeolite and acetic acid used in a batch chlorination process of toluene. The conversion of toluene was 99.8% and the selectivity of para-chlorotoluene was 70.2%. Another example involves L-type zeolite mixed with dichloroacetic acid in the chlorination of chlorobenzene. The conversion of chlorobenzene was 90.5% and the selectivity of para-dichlorobenzene was 92.7%.

Although the use of an aliphatic carboxylic acid as a co-catalyst with L-type zeolite can improve conversion and para selectivity of a chlorination reaction, it inevitably increases the raw material cost for making the chlorinated products. Furthermore, because of the need to separate aliphatic carboxylic acid from the final product after the completion of the reaction, substantial increase in equipment and production costs would incur.

SUMMARY OF THE INVENTION

The primary object of the present invention is to develop a heterogeneous catalytic chlorination process that eliminates many of the disadvantages of the prior art processes and improves the conversion from aromatic reactants as well as the para selectivity of the reaction products. The reaction products that can be produced from the technique disclosed in the present invention are represented by the following formula:

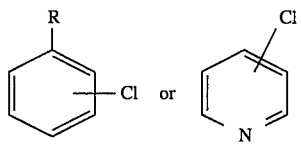

Wherein R can be an alkyl group having one to three carbons, or a floride, chloride, bromide, iodide, or hydroxyl group. The aromatic reactants can be a substituted benzene represented by the formula: $C_6H_5R$ (wherein $R=C_1-C_3$ alkyl, F, Cl, Br, I, or OH), or pyridine. Chlorine gas is used as a chlorination agent.

The present invention discloses a catalytic chlorination process that utilizes a highly active de-aluminated zeolite catalyst to improve para selectivity of chlorinated products from aromatic reactants. The process disclosed in the present invention can be operated over a wide range of reaction temperatures from approximately 25° to 250° C., and a wide range of reaction pressures from approximately 0.5 to 40 atm. The process disclosed in the present invention can also accommodate a wide range of flow rates, measured in terms of liquid hourly space velocity (LHSV), from approximately 0.01 to 10.0 $hr^{-1}$. The ratio between aromatic reactants and chlorine gas is preferably between 1/4 to 4/1. One of the main advantages of the process disclosed in the present invention is that no co-catalyst, such as aliphatic carboxylic acid disclosed in the prior art, is required to improve the para selectivity. Another advantage of the present invention is that the chlorination reaction can be conducted continuously in a fixed-bed type reactor. Reactants, which include the aromatic compounds and chlorine gas, can be continuously pumped into the fed bed reactor to effect the chlorination reaction and obtain chlorinated products with high para selectivity.

The zeolite catalyst disclosed in the present invention is a low-alumina content zeolite obtained by modifying an L-type zeolite, which is typically represented by the following formula:

$$K_9[(AlO_2)_9(SiO_2)_{27} \cdot 22H_2O]$$

It should be noted that the above formula only represents a typical L-type zeolite; the composition of L-type zeolites can vary, to some extent, depending on the source material and the processes used in making therefor. For example, the L-type zeolite used in the '722 patent has an silicon dioxide ($SiO_2$)/aluminum oxide ($Al_2O_3$) ratio in the range between 4 and 8. Furthermore, the L-type zeolite to be used as a starting material for making the low-alumina zeolite may contain a cation other than the potassium ion. For example, the potassium ion may be ion-exchanged with sodium by treating the potassium-containing L-type zeolite with an aqueous solution containing nitrate or chloride of sodium. The potassium ion in the L-type zeolite used in the present invention may also be ion-exchanged with a metal of the Group IA (other than sodium), IIA, IIIA, IVA, or VA in the periodic table. These cations may be included along or in combination with other cations in the zeolite. The preferred extent of ion-exchange is between 0.5 and 20 wt %.

The zeolite catalyst of the present invention is obtained by reducing the alumina content of the L-type zeolite described above through a de-alumination reaction. Examples of the de-alumination reactions used in the present invention to reduce the content of alumina from an L-type zeolite include: EDTA extraction, high-temperature treatment, and chemical vapor deposition (CVD) using $SiCl_4$, etc. The preferred $SiO_2/Al_2O_3$ ratio of the zeolite for use in the present invention ranges between 9/1 to 40/1.

DETAILED DESCRIPTION OF PREFERRED EMBODIMENTS

The present invention will now be described more specifically with reference to the following examples. It is to be noted that the following descriptions of examples including preferred embodiments of this invention are presented herein for purpose of illustration and description; it is not intended to be exhaustive or to limit the invention to the precise form disclosed.

EXAMPLE 1

A commercially available L-type zeolite having the composition as shown in Table 1 was obtained from N. E. Chemcat:

TABLE I

| Component | Weight percent (dry basis) |
|---|---|
| $Al_2O_3$ | 17.5% |
| $SiO_2$ | 63.3% |
| $K_2O$ | 13.0% |
| $Na_2O$ | 0.03% |

Molar ratio of $SiO_2/Al_2O_3$: 6.2

The L-type zeolite was pelletized into a 4 cm (W)×0.5 cm (D) pellet and then crushed and sieved to obtain 20–30 mesh particles. 0.8 g of the crushed zeolite particles were placed into a glass tube to form a fixed bed reactor. Hot air at 450° C. was flowed through the reactor for three hours to activate the catalyst. Thereafter, toluene was pumped into the reactor at 0.66 g/hr, and chlorine gas was simultaneously pumped into the reactor at 3.06 ml/min, representing a molar ratio between toluene and chlorine gas of 1:1. The two reactant streams were mixed and reacted in the reactor at a reaction temperature of 100° C. and a reaction pressure of 1 atm. The reaction products were collected and analyzed using a gas chromatography. The results, which are shown in Table 2, indicate a conversion of toluene of 85.6%, and selectivities for para- and ortho-chlorotoluenes of 32.4% and 40.4%, respectively.

In Table 2, as well as in subsequent tables and examples, the definitions of conversion, para-selectivity and ortho-selectivity are given by the following relationships:

$$\text{Conversion, mole \%} = \frac{A-B}{A} \times 100\% \quad (1)$$

Wherein:
A is the molar content of aromatic compound in the feed composition, and
B is the molar content of unreacted aromatic compound in the product 15 composition.

$$\text{para-selectivity, mole \%} = \frac{P}{A-B} \times 100\% \quad (2)$$

$$\text{ortho-selectivity, mole \%} = \frac{O}{A-B} \times 100\% \quad (3)$$

Wherein:
P is the molar content of the para-chlorine-substituted aromatic compound in the product composition, and O is the molar content of the ortho-chlorine-substituted aromatic compound in the product composition.

EXAMPLES 2 through 5

The reaction conditions in Examples 2 through 5 were identical to that in Example 1, except that the catalysts used were ZSM-5 zeolite, Y-type zeolite, Mordenite zeolite, and aluminum alumina phosphate, respectively. The results of the chlorination reaction of toluene from Examples 1 through 5 are listed in Table 2

TABLE 2

| Example No. | Catalyst | Conversion of toluene (%) | Selectivity of para-chlorotoluene (%) | Selectivity of ortho-chlorotoluene (%) |
|---|---|---|---|---|
| Example 1 | L-type zeolite | 82.3 | 34.2 | 46.3 |
| Example 2 | ZSM-5 zeolite | 69.5 | 31.5 | 48.6 |
| Example 3 | Y-type zeolite | 82.2 | 22.1 | 40.6 |
| Example 4 | Mordenite zeolite | 80.5 | 32.2 | 46.3 |
| Example 5 | aluminum alumina phosphate | 82.3 | 27.6 | 47.7 |

EXAMPLES 6 through 8

L-type zeolite was used in the chlorination reactions of toluene in Examples 6 through 9, whose reaction conditions were otherwise identical to that in Example 1, except for the changes as indicated, respectively, in Table 3. These changes in the reaction conditions include the feed rate of toluene, the feed rate of chlorine gas, the ratio of toluene/chlorine gas, and the reaction temperature. The reaction results are listed in Table 3.

TABLE 3

| Example No. | Reaction Temp. (C.) | toluene feed rate (g/hr) | chlorine gas feed rate (ml/hr) | molar ratio of toluene/chlorine | conversion of toluene (%) | Selectivity of parachlorotoluene (%) | Selectivity of orthochlorotoluene (%) |
|---|---|---|---|---|---|---|---|
| 6 | 60 | 0.66 | 3.06 | 1:1 | 93.9 | 32.3 | 45.3 |
| 7 | 80 | 0.66 | 3.06 | 1:1 | 91.9 | 37.4 | 47.2 |
| 1 | 100 | 0.66 | 3.06 | 1:1 | 82.3 | 34.2 | 46.3 |
| 8 | 60 | 1.32 | 3.06 | 2:1 | 49.9 | 51.1 | 44.3 |

EXAMPLE 9

A de-aluminated L-type zeolite was obtained by subjecting the L-type zeolite as used in Example 1 to a de-alumination reaction using an $H_4$EDTA extraction technique. 20 g of L-type zeolite and 9.06 g of $H_4$ EDTA were added into a 300 ml deionized water and mixed. The mixture was heated under a reflux for 16 hours, then filtered and rinsed with water three times. The residue was dried at 110° C. for three hours, and finally activated by flowing hot air at 450° C. therethrough for three hours.

The de-aluminated L-type zeolite was analyzed to the chemical composition as shown in Table 4:

TABLE 4

| Component | Weight percent (dry basis) |
|---|---|
| $Al_2O_3$ | 12.1% |
| $SiO_2$ | 71.0% |
| $K_2O$ | 11.9% |
| $Na_2O$ | 0.3% |

Molar ratio of $SiO_2/Al_2O_3$: 10.0

The de-aluminated L-type zeolite can also be obtained using other methods such as $Na_4$ EDTA extraction, steam hydrothermal processing, or $SiCl_4$ chemical vapor deposition.

The de-aluminated L-type zeolite obtained from the above procedure was also analyzed with X-ray diffraction, using CuK ct as the radiation source. The X-ray diffraction results are shown in Table 5.

TABLE 5

| Diffraction Angle, $2\theta$ (°) | Lattice Constant d (Å) | Relative Intensity ($I/I_o$) |
|---|---|---|
| 3.69 | 23.905 | 54 |
| 5.46 | 16.160 | 100 |
| 11.93 | 7.410 | 60 |
| 14.71 | 6.019 | 71 |
| 19.33 | 4.589 | 63 |
| 22.79 | 3.898 | 65 |
| 24.41 | 3.644 | 49 |
| 25.56 | 3.482 | 54 |
| 27.18 | 3.278 | 49 |
| 28.03 | 3.181 | 80 |
| 30.80 | 2.901 | 65 |

EXAMPLE 10

0.8 g of the de-aluminated L-type zeolite from Example 10 was pelletized, crushed and packed into a glass reactor in a procedure similar to that disclosed in Example 1. Toluene was pumped into the reactor at 1.32 g/hr, and chlorine gas was simultaneously pumped into the reactor at 3.06 ml/min, representing a molar ratio between toluene and chlorine gas of 2:1. The two reactant streams were mixed and reacted in the reactor at a reaction temperature of 60° C. and a reaction pressure of 1 arm. The reaction products were collected and analyzed using a gas chromatography. The results indicate a conversion from toluene of 53.5%, and selectivities for para- and ortho-chlorotoluenes of 52.9% and 36.1%, respectively.

EXAMPLE 11

The de-aluminated L-type zeolite from Example 9 was ion-exchanged or impregnated with metallic ions, which are sourced from salts of Group IA or IIA metals, or hydrogen ions, to improve its activity and para selectivity.

14.5 g of the de-aluminated L-type zeolite from Example 9 and 11 g of NaCl (Na/K molar ratio 3/1 ) were added to 200 ml water to effect an ion-exchange reaction, which continued at room temperature for three hours. The solution mixture was then filtered and rinsed with water until no chlorine ions were detected. Thereafter, the residue was dried at 110° C. for three hours and activated by flowing hot air at 450° C. for three hours.

EXAMPLE 12

0.8 g of the de-aluminated and ion-exchanged L-type zeolite from Example 11 was pelletized, crushed and packed into a glass reactor in a procedure similar to that disclosed in Example 10. Toluene was pumped into the reactor at 1.32 g/hr, and chlorine gas was simultaneously pumped into the reactor at 3.06 ml/min, representing a molar ratio between toluene and chlorine gas of 2:1. The two reactant streams were mixed and reacted in the reactor at a reaction temperature of 60° C. and a reaction pressure of 1 atm. The reaction products were collected and analyzed using a gas chromatography. The results indicate a conversion from toluene of 50.7%, and selectivities for para- and ortho-chlorotoluenes of 54.9% and 38.5%, respectively.

EXAMPLE 13

0.8 g of the de-aluminated L-type zeolite from Example 10 was pelletized, crushed and packed into a glass reactor in a procedure similar to that disclosed in Example 11. Chlorobenzene was pumped into the reactor at 1.764 g/hr, and chlorine gas was simultaneously pumped into the reactor at 3.06 ml/min, representing a molar ratio between chlorobenzene and chlorine gas of 2.3:1. The two reactant streams were mixed and reacted in the reactor at a reaction temperature of 60° C. and a reaction pressure of 1 atm. The reaction products were collected and analyzed using a gas chromatography. The results indicate a conversion of toluene of 80%, and selectivities for para- and ortho-dichlorobenzenes of 91.4% and 8.5%, respectively.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

We claim:

1. A high para-selectivity chlorination process for chlorinating aromatic reactant comprising the steps of:
   (a) obtaining a chlorination reactor containing a catalyst composition which comprises a de-aluminated zeolite, said de-aluminated zeolite catalyst having a $SiO_2/Al_2O_3$ ratio of between 9/1 to 40/1; and
   (b) feeding said aromatic reactants and chlorine gas into said reactor to effect said chlorination process to produce chlorinated aromatic products; wherein said aromatic reactant is either toluene or chloro-benzene, and said de-aluminated zeolite is an L-type zeolite that has been treated by a de-aluminating process to reduce aluminate content thereof;
   (c) further wherein said de-aluminating process comprises a $SiCl_4$ chemical vapor deposition step to reduce said aluminate content of said L-type zeolite.

2. The high para-selectivity chlorination process of claim 1 wherein said chlorination process is conducted at a reaction temperature between 25° and 200° C., a reaction pressure between 0.5 and 40 atm, and a liquid hourly space velocity between 0.01 and 10.0 $hr^{-1}$.

3. The high para-selectivity chlorination process of claim 1 wherein said chlorination process is conducted at a reaction temperature between 40° and 100° C., a reaction pressure between 0.5 and 5 atm, and a liquid hourly space velocity between 0.1 and 5.0 $hr^{-1}$.

4. The high para-selectivity chlorination process of claim 1 wherein said chlorination reactor is a fixed bed reactor.

5. The high para-selectivity chlorination process of claim 1 wherein said chlorination reactor is a batch type reactor.

6. The high para-selectivity chlorination process of claim 1 wherein said chlorination reaction having a feed ratio between said aromatic reactants and said chlorine gas of between 1/4 and 4/1.

7. The high para-selectivity chlorination process of claim 1 wherein said de-aluminated zeolite has a $SiO_2/Al_2O_3$ ratio between 10 and 20.

8. The high para-selectivity chlorination process of claim 1 wherein said de-aluminating process comprises an H4 EDTA extraction step to reduce said aluminate content of said L-type zeolite.

9. The high para-selectivity chlorination process of claim 1 wherein said de-aluminating process comprises a $Na_4$ EDTA extraction step to reduce said aluminate content of said L-type zeolite.

10. A high para-selectivity chlorination process for chlorinating aromatic reactant comprising the steps of:
    (a) obtaining; a chlorination reactor containing a catalyst composition which comprises a de-aluminated zeolite, said de-aluminated zeolite catalyst having a $SiO_2/Al_2O_3$ ratio of between 9/1 to 40/1; and
    (b) feeding said aromatic reactants and chlorine gas into said reactor to effect said chlorination process to produce chlorinated aromatic products; wherein said aromatic reactant is either toluene chloro-benzene; and said de-alumino ted zeolite is an L-type zeolite that has been treated by a de-alminating process to reduce aluminate content thereof;
    (c) wherein said de-aluminating process comprises an ion-exchange process with Group IA or Group IIA metal ions or hydrogen ions.

11. The high para-selectivity chlorination process of claim 10 wherein the extent of ion exchanged is between about 0.5 and about 20 weight percent.

12. The high para-selectivity chlorination process of claim 1 wherein said catalyst composition consists essentially of a de-aluminated zeolite having a $SiO_2/Al_2O_3$ ratio from 9/1 to 40/1.

13. The high para-selectivity chlorination process of claim 10 wherein said chlorination process is conducted at a reaction temperature between 25° and 200° C., a reaction pressure between 0.5 and 40 atm, and a liquid hourly space velocity between 0.01 and 10.0 $hr^{-1}$.

14. The high para-selectivity chlorination process of claim 10 wherein said chlorination process is conducted at a reaction temperature between 40° and 100° C., a reaction pressure between 0.5 and 5 arm, and a liquid hourly space velocity between 0.1 and 5.0 hr$^{-1}$.

15. The high pars-selectivity chlorination process of claim 1 wherein said chlorination reaction having a feed ratio between said aromatic reactants and said chlorine gas of between 1/4 and 4/1.

16. The high pars-selectivity chlorination process of claim 1 wherein said de-aluminated zeolite has a $SiO_2/Al_2O_3$ ratio between 10 and 20.

* * * * *